(12) United States Patent
Frank et al.

(10) Patent No.: US 10,416,177 B2
(45) Date of Patent: Sep. 17, 2019

(54) ANALYSIS SYSTEM FOR A BIOLOGICAL SAMPLE

(71) Applicant: Roche Molecular Systems, Inc., Pleasanton, CA (US)

(72) Inventors: Paul Frank, Ennetbuergen (CH); Christopher Newhouse, Mendham, NJ (US); Sascha Roehrig, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 14/244,059

(22) Filed: Apr. 3, 2014

(65) Prior Publication Data

US 2014/0370609 A1   Dec. 18, 2014

(30) Foreign Application Priority Data

Apr. 5, 2013   (EP) .................... 13162469

(51) Int. Cl.
*G01N 35/00* (2006.01)
*G16H 10/40* (2018.01)

(52) U.S. Cl.
CPC . *G01N 35/00732* (2013.01); *G01N 35/00871* (2013.01); *G16H 10/40* (2018.01); *G01N 2035/00811* (2013.01); *G01N 2035/00831* (2013.01); *Y10T 436/115831* (2015.01)

(58) Field of Classification Search
CPC ....... G01N 35/00732; G01N 35/00722; G01N 35/00584; G01N 35/00871; G01N 2035/00811; G01N 2035/00831; Y10T 436/115831; Y10T 436/11; Y10T 436/00
USPC .......... 436/50, 43, 67, 63; 422/67, 63, 50, 43
See application file for complete search history.

(56) References Cited

U.S. PATENT DOCUMENTS

| 8,035,485 B2 | 10/2011 | Fritchie | |
|---|---|---|---|
| 2006/0148063 A1* | 7/2006 | Fauzzi | G01N 1/31 435/286.4 |
| 2008/0213872 A1 | 9/2008 | Regan | |
| 2008/0228589 A1 | 9/2008 | Kochler et al. | |
| 2009/0088336 A1 | 4/2009 | Burd et al. | |
| 2010/0062521 A1 | 3/2010 | Veriac et al. | |
| 2011/0093249 A1 | 4/2011 | Holmes et al. | |

FOREIGN PATENT DOCUMENTS

| EP | 1188126 B1 | 4/2005 |
|---|---|---|
| EP | 2282211 A1 | 2/2011 |
| JP | 2010540971 A | 12/2010 |
| WO | WO2010084921 A1 | 7/2010 |

OTHER PUBLICATIONS

Roche "AMPLILINK Software Version 3.3 Series, Utility Channel Supplement Version 1.1 for Use With COBAS TaqMan 48 analyzer".

\* cited by examiner

*Primary Examiner* — Christine T Mui (74) *Attorney, Agent, or Firm* — Pamela C. Ancona; David J. Chang (57) ABSTRACT

The invention provides for an analysis system (100, 300, 400) for analyzing a biological sample (108) comprising an analyzer (102) with an analytical unit (106) for analyzing the biological sample to obtain an analysis result (140). The analyzer is configured for receiving a cartridge (110) comprising an identifier (114) and containing at least one reagent for analyzing the biological sample. The analyzer comprises an identification unit (116) for reading the identifier. The analyzer accepts the cartridge if the identifier is valid. The analysis system further comprises a protocol creation system (150, 104). Instructions cause the protocol creation system to: receive (200) analysis protocol parameters (164) from a user interface (158); generate (202) a custom analysis protocol (138) using the analysis protocol parameters; link (204) the custom analysis protocol to an invalid identifier which changes the invalid identifier into a valid identifier, and transfer (206) the user created analysis protocol associated with the now valid identifier to the analyzer controller.

9 Claims, 9 Drawing Sheets

ANALYSIS SYSTEM FOR A BIOLOGICAL SAMPLE

CROSS-REFERENCES TO RELATED APPLICATIONS

The present application claims the benefit of priority under 35 U.S.C. § 119(a) of EP13162469.4, filed Apr. 5, 2013, the entire contents of which is hereby incorporated by reference.

FIELD OF THE INVENTION

The invention relates to analysis systems for analyzing biological samples, in particular it relates to the creation of custom analysis protocols in fully automated analytical high throughput systems.

BACKGROUND

Fully automated diagnostic analytical systems rely on validated assays and/or workflows. However in many situations, it would be beneficial if laboratories could specify custom assays for such fully automated diagnostic analyzer systems. For example to develop assays to detect emerging epidemics or for performing research studies.

U.S. Pat. No. 8,035,485 discloses a system for automation of laboratory analyzers that utilizes radio frequency identification tags.

United States patent application US 2009/0088336 A1 discloses a cartridge for automated detection on an analyte in a body fluid comprising: a sample collection unit configured to receive the bodily fluid sample, and array of assay units configured to receive a portion of the sample collection unit and run a chemical reaction that yields a detectible signal indicative of the presence of the analyte; an array of reagent units containing reagents for running the chemical reaction.

United States patent application 2008/0213872 A1 discloses cartridges which are inserted into the housing areas of flow-through automated instruments, which are equipped with sensors to ensure proper placement and usage of the cartridges. This application further discloses that cartridges may be identified with bar codes to prevent inserting the wrong cartridge or re-use of a cartridge and that a warning that the system may notify a user.

United States patent application 2011/0093249 A1 discloses a device which is also referred to as a cartridge. The device comprises a housing with location to accommodate assay units and reagent units. This application further discloses that many different sequences can be run for any chemical reaction to run on the device and that this may be done without changing the type of reagents in the cartridge. This application further discloses that the device may have an identifier that is detected or read by an identifier detector.

SUMMARY

The invention provides for an analysis system and a method in the independent claims. Embodiments are given in the dependent claims.

In one aspect, the invention provides for an analysis system for analyzing a biological sample comprising, a cartridge comprising an identifier and containing at least one reagent for analyzing the biological sample; an analyzer, wherein the analyzer comprises an analytical unit for analyzing the biological sample to obtain an analysis result, wherein the analyzer comprises an analyzer controller, wherein the analyzer is configured for receiving the cartridge, wherein the analyzer comprises an identification unit for reading the identifier, wherein the analyzer controller comprises a controller memory containing a set of analysis protocols, wherein the analyzer is configured for checking the validity of the identifier using the identification unit by comparing the identifier to the set of analysis protocols, wherein the analyzer is configured for accepting the cartridge if the identifier is valid, wherein the analyzer is configured for rejecting the cartridge if the identifier is invalid, wherein each of the set of analysis protocols defines protocols and parameters for performing an analysis of the biological sample and is referenced by a protocol identifier, wherein the analyzer controller is configured for receiving the identifier from the identification unit; a protocol creation system comprising a processor, wherein the protocol creation system further comprises a protocol creation system memory containing machine executable instructions; wherein execution of the machine executable instructions causes the processor to receive analysis protocol parameters from a user interface, generate a custom analysis protocol using the analysis protocol parameters, link the custom analysis protocol to a protocol identifier, and changing an invalid identifier on the cartridge into a valid identifier by appending the user created analysis protocol associated with the protocol identifier to the set of analysis protocols in the analyzer controller if the invalid identifier corresponds to the protocol identifier; and wherein the analyzer controller accepts the cartridge comprising the now valid identifier which permits the biological sample to be processed according to the custom analysis protocol using the cartridge comprising the now valid identifier in the analyzer.

In another aspect, the invention provides for a method of analyzing a biological sample in an automated analysis system comprising an analyzer, wherein the analyzer is configured for accepting a cartridge with a valid identifier and rejecting a cartridge with an invalid identifier, comprising the steps of, a) providing a cartridge comprising an invalid identifier and containing at least one reagent for analyzing the biological sample; b) generating a custom analysis protocol with a protocol creation system, wherein steps a) and b) are interchangeable or may be performed in parallel; c) linking the custom analysis protocol to a protocol identifier corresponding to the invalid identifier; d) changing the invalid identifier into a valid identifier by transferring the custom analysis protocol associated with the protocol identifier from the protocol creation system to a set of analysis protocols stored by an analyzer controller of the analyzer, wherein the analyzer controller comprises a controller memory containing the set of analysis protocols, wherein the analyzer controller permits the analyzer to accept the cartridge if the invalid identifier corresponds to the protocol identifier by comparing the identifier to the set of analysis protocols; e) selecting the custom analysis protocol linked to the protocol identifier corresponding to the now valid identifier, f) loading the cartridge into the automated analyzer; g) reading the identifier, wherein the identifier is read by an identification unit comprising an identifier reader comprised in the analyzer; and h) analyzing the biological sample using at least one aliquot of the at least one reagent comprised in the cartridge according to the selected custom analysis protocol.

BRIEF DESCRIPTION OF THE FIGURES

In the following embodiments of the invention are explained in greater detail, by way of example only, making reference to the drawings in which.

DETAILED DESCRIPTION OF THE INVENTION

Definitions

A controller as used herein encompasses a device, machine, or apparatus for controlling the operation and/or function of one or more other devices. Examples of a controller may include, but are not limited to: a computer, a processor, an embedded system or controller, a programmable logic controller, and a microcontroller. A 'computing device' or 'computer' as used herein encompasses to any device comprising a processor. A 'processor' as used herein encompasses an electronic component which is able to execute a program or machine executable instruction.

A 'computer-readable storage medium' as used herein encompasses any tangible storage medium which may store instructions which are executable by a processor of a computing device. The computer-readable storage medium may be referred to as a computer-readable non-transitory storage medium.

'Computer memory' or 'memory' is an example of a computer-readable storage medium. Computer memory is any memory which is directly accessible to a processor or other controller.

'Computer storage' or 'storage' is an example of a computer-readable storage medium. Computer storage is any non-volatile computer-readable storage medium.

A 'user interface' as used herein is an interface which allows a user or operator to interact with a computer or computer system.

A 'hardware interface' as used herein encompasses a interface which enables a processor or other controller to interact with and/or control an external computing device and/or apparatus. A hardware interface may allow a processor to send control signals or instructions to an external computing device and/or apparatus. The hardware interface may enable the processor or other controller to receive sensor data and control the dispensing of the fluid. The hardware interface may be used to form a closed control loop in some embodiments.

A 'biological sample' as used herein, refers to a material suspected of containing an analyte of interest. The sample can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, distillation, concentration, inactivation of interfering components, and the addition of reagents. A sample may be used directly as obtained from the source or following a pretreatment to modify the character of the sample, e.g. after being diluted with another solution or after having being mixed with reagents e.g. to carry out one or more diagnostic assays like e.g. clinical chemistry assays, immunoassays, coagulation assays, nucleic acid testing, and etc. The term "sample" as used herein is therefore not only used for the original sample but also relates to a sample which has already been processed (pipetted, diluted, mixed with reagents, enriched, having been purified, having been amplified etc). As used herein, the term "analyte" refers to the compound or composition in the biological sample to be detected or measured.

The term 'reagent' is used to indicate a composition required for treatment of a sample. Reagents may be any liquid, e.g. a solvent or chemical solution, which needs to be mixed with a sample and/or other reagent in order e.g. for a reaction to occur, or to enable detection. A reagent may be for example a diluting liquid, including water, it may comprise an organic solvent, it may comprise a detergent, it may be a buffer. Reagents may also be dry reagents adapted e.g. to be dissolved by a sample, another reagent or a diluting liquid. A reagent in the more strict sense of the term may be a liquid solution containing a reactant, typically a compound or agent capable e.g. of binding to or chemically transforming one or more analytes present in a sample. Examples of reactants are enzymes, enzyme substrates, conjugated dyes, protein-binding molecules, nucleic acid binding molecules, antibodies, chelating agents, promoters, inhibitors, epitopes, antigens, and etc.

In one aspect the invention provides for an analysis system for analyzing a biological sample. The analysis system comprises an analyzer. The analyzer comprises an analytical unit for analyzing the biological sample to obtain an analysis result. The analytical unit may perform a measurement on the biological sample to obtain the analysis result. As used herein an analyzer may also refer to multiple analyzers. Also an analytical unit may also refer to one or more analytical units. As such the analysis system may comprise more than one analyzer and each analyzer may comprise more than one analytical unit.

The term 'measurement' relates to any type of measurement that can be performed on a biological sample following addition of at least one reagent, either directly or after processing of the biological sample. Processing of the biological sample may include isolating and/or purifying the analyte. In one embodiment, the reagents used for measurement may be analyte specific.

The term 'analysis result' relates to the result of the analysis. The analysis result is obtained based on the measurement of the biological sample. The analysis result may be qualitative (the amount of analyte is above or below a threshold) or quatitative.

The analyzer comprises an analyzer controller. The analyzer is operable or configured for receiving a cartridge comprising an identifier. An identifier is a property or label or tag which enables a cartridge to be identified as a specific cartridge or as a particular class of cartridge.

In some embodiments the identifier may be a tag such as a barcode or RFID tag.

In other embodiment the identifier may also comprise such properties as the dimensions or color of the cartridge. The cartridge contains at least one reagent for analyzing the biological sample. The analyzer comprises an identification unit for reading the identifier. The identification unit of course depends upon the type of identifier, for instance if the identifier is an RFID chip then the identification unit may comprise something for reading the RFID chip. Likewise, if the identifier comprises a barcode then the identification unit comprises a barcode reader. If the identifier is loaded to the shape or dimensions or color of the cartridge then the identification unit comprises an apparatus operable or configured for reading or measuring this property. The analyzer is operable or configured for receiving the cartridge.

The analyzer is operable or configured for checking the validity of the identifier using the identification unit. The validity may for instance be compared or checked by comparing the identifier to a list of valid cartridges or protocol identifiers. The system is operable or configured for accepting the cartridge if the identifier is valid. The analyzer controller comprises a controller memory containing a set of analysis protocols. Each of the set of analysis protocols defines protocols and parameters for performing an analysis of the biological sample and is referenced by a protocol identifier.

The term 'protocol' relates to the conditions in the analytical system to which the biological sample is subjected in order to obtain the analysis result.

The term 'parameters' or 'protocol parameters' relates to the parameters defining a protocol.

The analyzer controller is operable or configured for receiving the identifier from the identification unit. If the cartridge does not have a valid identifier then the analyzer may reject the use of the cartridge and not allow an analysis of the biological sample to be performed.

The analysis system further comprises a protocol creation system comprising a processor. The protocol creation system further comprises a protocol creation system memory containing machine-executable instructions. The protocol creation system memory is computer memory or storage. Execution of the machine-executable instructions causes the processor to receive analysis protocol parameters from a user interface. For instance an operator may enter data or parameters into the user interface which are able to be used to generate the analysis protocol.

Execution of the machine-executable instructions further cause the processor to generate a custom analysis protocol using the analysis protocol parameters. Execution of the instructions further causes the processor to link a custom analysis protocol to a protocol identifier. Execution of the machine-executable instructions further causes the processor to transfer the user created analysis protocol associated with the protocol identifier to the analyzer controller. The transfer of the user created analysis protocol associated with the protocol identifier to the analyzer controller then changes an invalid identifier of a specific cartridge into a valid identifier if the invalid identifier corresponds to the protocol identifier.

The analyzer controller is operable or configured to append the custom analysis protocol to the set of analysis protocols.

The analyzer controller accepts the cartridge comprising the now valid identifier which enables the biological sample to be processed according to the custom analysis protocol. This may be accomplished using the cartridge comprising the now valid identifier in the analyzer.

This embodiment is advantageous because it enables the analyzer to load cartridges and perform custom analysis protocol that the analyzer would not be able to load. For instance many analysis systems used in laboratories have specific tests which are specified and certified. Their architecture prevents them from being used in a way which is not specified. Embodiments of the invention may provide for a convenient means of enabling custom cartridges and/or custom analysis protocols to be performed on such an analysis system.

The term 'identifier' relates to an identifier of a cartridge as described herein.

The term 'protocol identifier' relates to a identifier to which a protocol may be linked and which corresponds to an identifier of a cartridge.

The transfer of the user created analysis protocol associated with the protocol identifier to the analyzer controller may be performed in a number of different ways. For instance in one embodiment the transfer may occur across a network.

In another embodiment the user created analysis protocol may be written onto storage on a cartridge such as an RFID chip which is then transferred via the cartridge to the analyzer.

In another embodiment the analyzer controller comprises a controller memory containing a set of analysis protocols.

In another embodiment the analyzer controller comprises a controller memory containing a set of analysis protocols.

In another embodiment the analyzer is configured for checking the validity of identifier using the identification unit by comparing the identifier to the set of analysis protocols. The analyzer is configured to accept the cartridge if the identifier is valid. The analyzer is configured to reject the cartridge if the identifier is invalid. The analyzer may determine if the identifier is valid or invalid by checking so see if the identifier is one of or is listed in the set of analysis protocols. If the identifier is one of the set of analysis protocols then it is valid. If the identifier is not one of the set of analysis protocols then it is invalid.

In another embodiment execution of the instructions cause the processor to change an invalid identifier on the cartridge into a valid identifier by appending the user created analysis protocol associated with the protocol identifier to the set of analysis protocols in the analyzer controller. In some cases this may be done if the invalid identifier corresponds to the protocol identifier. This may then result in the analyzer controller accepting the now valid identifier which permits the biological sample to be processed according to the custom analysis protocol using the cartridge comprising valid identifier in the analyzer. This has turned an invalid identifier into a valid identifier.

The combination of the above mentioned embodiments may provide for a means of expanding the functionality of an analysis system which comprises an analytical unit and controls the selection of analysis protocols with an identifier on a cartridge filled with a reagent In another embodiment a data carrier such as a computer-readable storage medium such as a contact disc or USB stick may have the analysis protocol written to it. An operator may then later transfer it to the analyzer.

In a further embodiment the analyzer and the protocol creation system are integrated into a single computer or computer system. In this case the transfer may occur by transferring data between the programs or by running a data file to the storage on the analyzer controller.

In another embodiment the protocol creation system is operably linked to the analyzer controller. Operably linked as used herein encompasses the ability between the protocol system and the analyzer controller to share data or functionality and enables them to be operated in conjunction with one another. For instance there may be a network connection between the protocol creation system and the analyzer controller.

In another embodiment the identifier comprises an identification tag. The identification unit comprises an identification tag reader. In this embodiment a tag of some sort is installed or attached onto the cartridge. The identification unit then at least partially uses the identification tag reader to read the identifier from the identification tag.

In another embodiment the identification tag comprises an RFID tag. In this case the identification unit would comprise an RFID reader.

In another embodiment the identifier is a unique identifier.

In another embodiment the protocol creation system comprises identification tag generator for generating a custom identification tag. The identification tag generator may for instance be a system producing a tag which may be attached to the cartridge. In other instances the identification tag generator is a system for modifying an existing tag. For instance the cartridge may comprise an RFID chip which is simply programmed by the identification tag generator. Execution of the machine-executable instructions further causes the processor to generate a custom identification tag comprising an identifier before linking the custom analysis protocol to the identifier.

In another embodiment the custom identification tag comprises an RFID tag. The identification tag generator comprises a first RFID interface. The protocol creation system is operable or configured for writing RFID data to the RFID tag using the first RFID interface. The identification tag reader comprises a second RFID interface. The analyzer controller is operable or configured for determining the identifier at least partially by reading the RFID data using the second RFID interface.

In another embodiment the identification tag generator is operable or configured for writing the RFID data to the RFID tag via a first cryptographic data exchange. The identification tag reader is operable or configured for reading the RFID tag via a second cryptographic data exchange. For instance a public key pair or an encryption key which is shared between the analysis system and the protocol creation system may be used to securely read and write data from the RFID tag. This may have the benefit of preventing someone from producing an unauthorized cartridge or custom analysis protocol.

The cryptographic data exchange could be performed in a variety of ways, for example the protocol creation system could generate a symmetric key that is used to encrypt the RFID data and then transmit the symmetric key to the analyzer. In another example the workflow manager generates a public key pair or uses a pre-existing key pair for the RFID tag which is then used to encrypt the data. The analyzer controller and the RFID chip use each other's public key to exchange data. In another example a key exchange is done. For example a Diffie-Hellman algorithm is used to exchange keys securely and then they use their keys to communicate securely via the RFID chip.

In another embodiment the RFID data comprises analysis protocol modification data. Analysis protocol modification data as used herein encompasses data which may be used to generate or modify an analysis protocol. For instance the custom analysis protocol could be stored on the RFID chip. In some embodiments the use of the first and second cryptographic data exchange may be used to verify that the protocol modification data on the RFID tag or chip is indeed valid and is allowed to create a custom analysis protocol on the analyzer.

In another embodiment the identifier is determined as least partially using the unique identifier.

In another embodiment the analyzer is an automated nucleic acid analyzer system.

In another embodiment the analysis system protocol parameters comprise any one of the following: an analysis protocol identifier, an identifier, a channel target assignment, an internal control validity range, a sample type, a sample process input volume, a polymerase chain reaction profile, a calculation sensitivity, dilution factors, incubation time, reagent addition, volumes, temperature settings, washing steps and combinations thereof.

The advantage of the system and method described herein is that it allows the operator to run custom made assays on a fully automated and validated analytical system. The present invention allows the operator to run custom made assays on a validated high throughput analytical system which supports sample pipetting from primary/secondary tubes, analyte isolation, preparation of analyte specific reagents, measurement and calculation to obtain an analysis result. The analytical system and method described herein also provide increased flexibility and optimized throughput which make it possible to react to seasonal or new occurrences of infectious diseases to which no validated assay reagents are offered for a specific high throughput system.

A further advantage is that the operator can use validated reagents which lack the analyte specific components to prepare the analyte specific reagents. This optimized the quality of the custom made analyte specific reagents and, thus, also optimizes the quality of the analysis results obtained by the operator.

In another embodiment the analyzer is an immunoassay analyzer or a coagulation analyzer or a nucleic acid analyzer.

The advantage of the present invention is that it allows the operator to run custom made assays on a fully automated and validated analytical system. The present invention allows the operator to run custom made assays on an analytical and fully integrated nucleic acid testing system which supports sample pipetting from primary/secondary tubes, nucleic acid isolation, preparation of specific amplification reagents, amplification and detection, calculation and export of intermediate results, reporting of analysis results and release of analysis results to an LIS and/or HIS system.

The term "amplification" generally refers to the production of a plurality of nucleic acid molecules from a target nucleic acid wherein primers hybridize to specific sites on the target nucleic acid molecules in order to provide an inititation site for extension by a polymerase.

Amplification can be carried out by any method generally known in the art, such as but not limited to: standard PCR, long PCR, hot start PCR, qPCR, RT-PCR, real time PCR and Isothermal Amplification such as 3SR, NASBA or TMA/TAA.

In another embodiment the identifier uniquely identifies a particular cartridge.

In another embodiment the identifier of the cartridge uniquely identifies a particular cartridge.

In another embodiment the identifier of the cartridge uniquely identifies the cartridge.

In another embodiment the identifier specifies a chosen analysis protocol. The chosen analysis protocol is one of the set of analysis protocols.

In another embodiment the custom identification tag comprises a barcode. The identification tag generally comprises a barcode printer. The identification tag reader comprises a barcode reader. The analyzer controller is operable or configured for determining the identifier at least partially from the barcode.

In another embodiment the analytical system further comprises the cartridge.

In another embodiment the cartridge comprises the identifier and also contains at least one reagent for analyzing the biological sample.

In another embodiment the at least one reagent comprises an assay specific reagent provided by an operator. In some embodiments the assay specific target reagent is provided by the operator and may be added to an empty cartridge by the operator. The cartridge may also further contain reagents which are not assay specific, that is they may be used for any assay also assays which are not specific for the used program by the operator.

Some specific examples of assay specific reagents are specific oligonucleotides for amplifying and/or detecting a target nucleic acid. They may also be specific antibodies but may also be other reagents used in the special assay such as enzymes, a cation or a detergent.

In another embodiment the analysis system further comprises a network connection for exchanging analysis protocol data between the protocol creation system and the analysis controller. Execution of the machine-executable instructions causes the processor to transfer the user created analysis protocol to the analyzer using the network connection.

In another aspect the invention provides for a method of analyzing a biological sample in an automated analysis system comprising an analyzer. The analyzer is operable or configured for accepting a cartridge with a valid identifier and rejecting a cartridge with an invalid identifier. The method comprises the step of providing a cartridge comprising an invalid identifier and containing at least one reagent for analyzing the biological sample. The method further comprises the step of generating a custom analysis protocol with a protocol creation system. The method further comprises the step of linking the custom analysis protocol to a protocol identifier corresponding to the invalid identifier. The method further comprises the step of transferring the custom analysis protocol with the protocol identifier from the protocol creation system to an analyzer controller of the analyzer, thereby changing the invalid identifier on the cartridge into a valid identifier.

The analyzer controller permits the analyzer to accept the cartridge with the now valid identifier. The method further comprises the step of selecting the custom analysis protocol linked to the protocol identifier corresponding to the now valid identifier. The method further comprises the step of loading the cartridge with the now valid identifier into the automated analyzer. The method further comprises the step of reading the identifier. The identifier is read by an identification unit. The analyzer comprises the identification unit. The method further comprises the step of analyzing the biological sample using at least one aliquot of said at least one reagent comprised in said cartridge according to the selected custom analysis protocol. It should be noted that the steps of providing the cartridge comprising an invalid identifier and containing at least one reagent for analyzing the biological sample and generating a custom analysis protocol with a protocol creation system are interchangeable and may be performed in parallel.

The term 'aliquot of a reagent' relates to portions of a reagent which are employed for testing of a biological sample. Aliquots are typically generated by pipetting a portion of a reagent into a tube or cuvette or well where then further treatment is conducted. When two or more aliquots of a reagent are needed it is for example possible to aspirate a volume of that reagent and to discharge portions of that volume into two or more wells. The term reagent aliquot is intended to cover also reagent aliquots mixed with biological samples and other fluids as it is typically necessary for assaying the biological samples.

In another embodiment the identifier comprises an identification tag.

In another embodiment the identifier is a unique identifier on the identification tag. The controller memory comprises a cross table comprising protocol identifiers corresponding to unique identifiers which assigns the unique identifier to the analysis protocol.

In another embodiment the identifier is generated on an identification tag by an identifier generator and the custom analysis protocol is stored with a reference to the protocol identifier.

In another embodiment the step of generating the custom analysis protocol with a protocol creation system comprises receiving analysis protocol parameters from the user interface, generating said custom analysis protocol using the analysis protocol parameters and linking the custom analysis protocol to a protocol identifier.

In another embodiment the custom analysis protocol is created on a protocol creation system. The custom created analysis protocol is transferred from the analysis protocol creation system to the analyzer controller using a network connection. The custom analysis protocol is referenced by the protocol identifier.

In another embodiment the method further comprises adding at least one reagent to the cartridge prior to providing the cartridge comprising invalid identifier and containing at least one reagent for analyzing the biological sample.

In another embodiment the steps of transferring said custom analysis protocol associated with the protocol identifier from the protocol creation system to an analyzer controller of the analyzer to the step of transferring the identifier to said analyzer controller are fully automated.

In another embodiment the at least one reagent comprises oligonucleotides specific for a target nucleic acid.

It is understood that one or more of the aforementioned embodiments of the invention may be combined as long as the combined embodiments are not mutually exclusive.

DETAILED DESCRIPTION

Like numbered elements in these figures are either equivalent elements or perform the same function. Elements which have been discussed previously will not necessarily be discussed in later figures if the function is equivalent.

Figure 1:
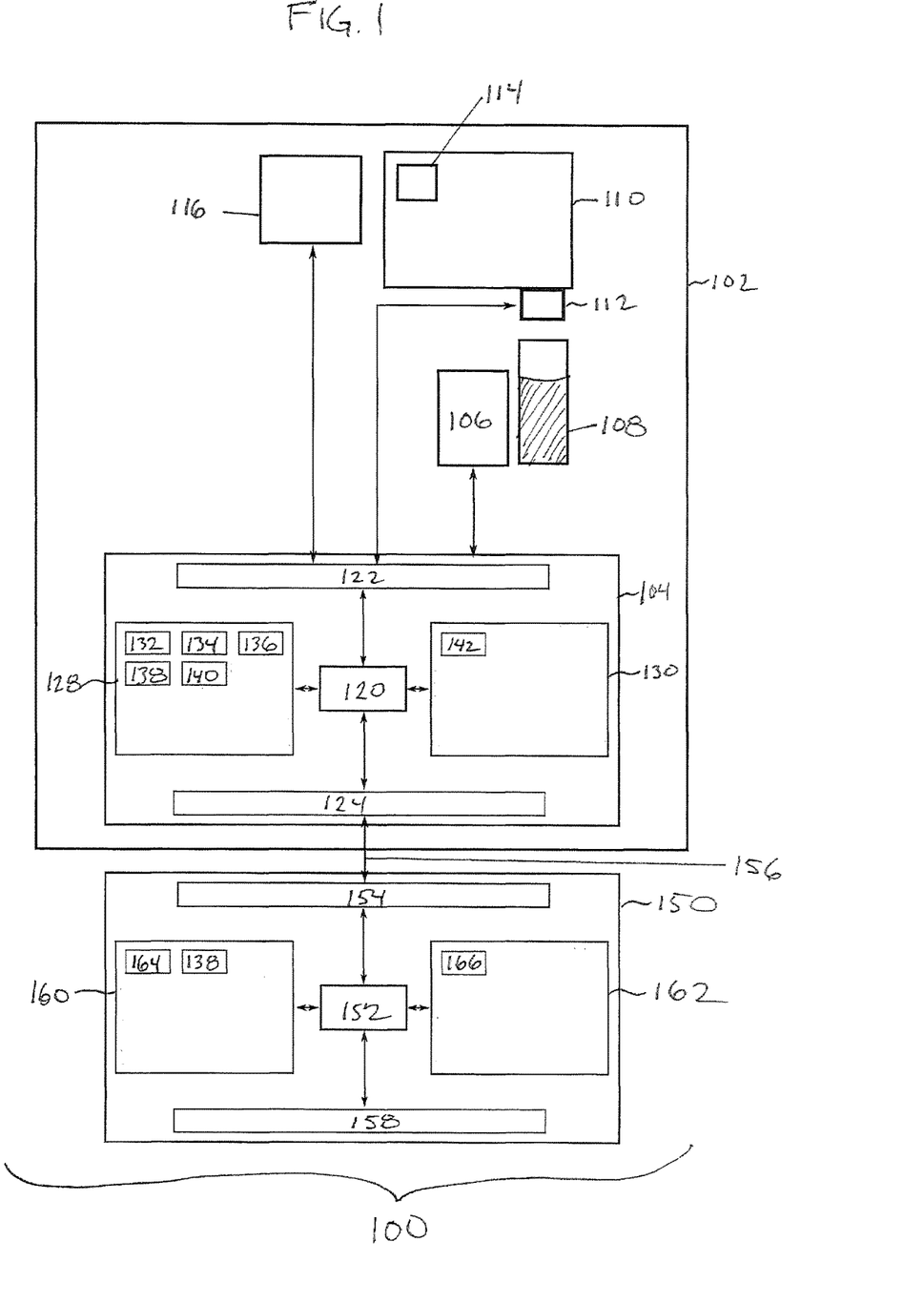
FIG. 1 shows an example of an analysis system with a protocol creation system.

FIG. 1 shows an example of an analysis system 100. The analysis system 100 comprises an analyzer 102. The analyzer 102 comprises an analyzer controller 104, an analytical unit 106, a dispenser 112 for cartridge 110 and an identification unit 116. It can be seen that there is a biological sample 108 adjacent to the analytical unit 106. The analytical unit 106 is operable or configured for obtaining an analysis result by performing a measurement on the biological sample 108. A cartridge 110 is seen as being installed into the analyzer 102. The cartridge 110 contains at least one reagent for analyzing the biological sample 108. The cartridge 110 is shown as being in connection with a dispenser 112 for dispensing the at least one reagent into the biological sample 108.

The cartridge 110 also has an identifier 114. In different embodiments this could be a tag, a barcode, an RFID chip, or other parameter which can be measured. There is an identification unit 116 for measuring or obtaining the identifier 114 from the cartridge 110. The analytical unit 106, the dispenser 112, and the identification unit 116 are all connected to a hardware interface 122 of the analyzer controller 104. The analyzer controller 104 further comprises a processor 120. The processor 120 is in communication with the hardware interface 122, a network interface 124, computer storage 128, and computer memory 130. The computer storage 128 is shown as containing a cartridge database 132.

The cartridge database 132 contains information on cartridges with valid identifiers. The computer storage 128 is shown as further containing an analysis protocol database 134. The analysis protocol database 134 contains a set of analysis protocols which may be used by the analyzer 102 for analyzing the biological sample 108 for a particular cartridge. There may be a linking between the various cartridges in the cartridge database 132 and the analysis protocol database 134. The computer storage 128 is shown as further containing an identifier 136. The identifier 136 has been read from the identifier 114 and the cartridge 110 by the identification unit 116. The identifier 136 may be checked against the cartridge database 132 to determine if a cartridge is valid or not. If it is valid then an associated analysis protocol is found in the analysis protocol database 134.

Computer storage 128 is further shown as containing a custom analysis protocol 138. The custom analysis protocol 138 was constructed using the protocol creation system 150. The computer storage 128 is further shown as containing an analysis result 140 that was measured by the analytical unit 106 from the biological sample 108.

The computer memory 130 is further shown as containing a control module 142. The control module 142 enables the processor 120 to control the operation and function of the analyzer 102. In particular the control module 142 may use the analysis protocol to control the analytical unit 106 to acquire the analysis result 140.

The analysis system 100 is further shown as comprising a protocol creation system 150. The protocol creation system 150 comprises a network interface 154. There is a network connection connecting the network interfaces 154 to 124. The protocol creation system 150 further comprises a processor 152. The processor 152 is in connection with the network interface 154, a user interface 158, computer storage 160 and computer memory 162. The computer storage 160 is shown as containing analysis protocol parameters 164 that have been received from the user interface 158. The analysis protocol parameters 164 were then used to create the custom analysis protocol 138 which is also shown as being stored in the computer storage 160. The custom analysis protocol 138 was transferred via the network connection 156 to the analyzer controller 104. The computer memory 162 is shown as containing analysis protocol creation module 166 which contains executable code which enables the processor 152 to create the custom analysis protocol 138 using the analysis protocol parameters 164.

Figure 2:
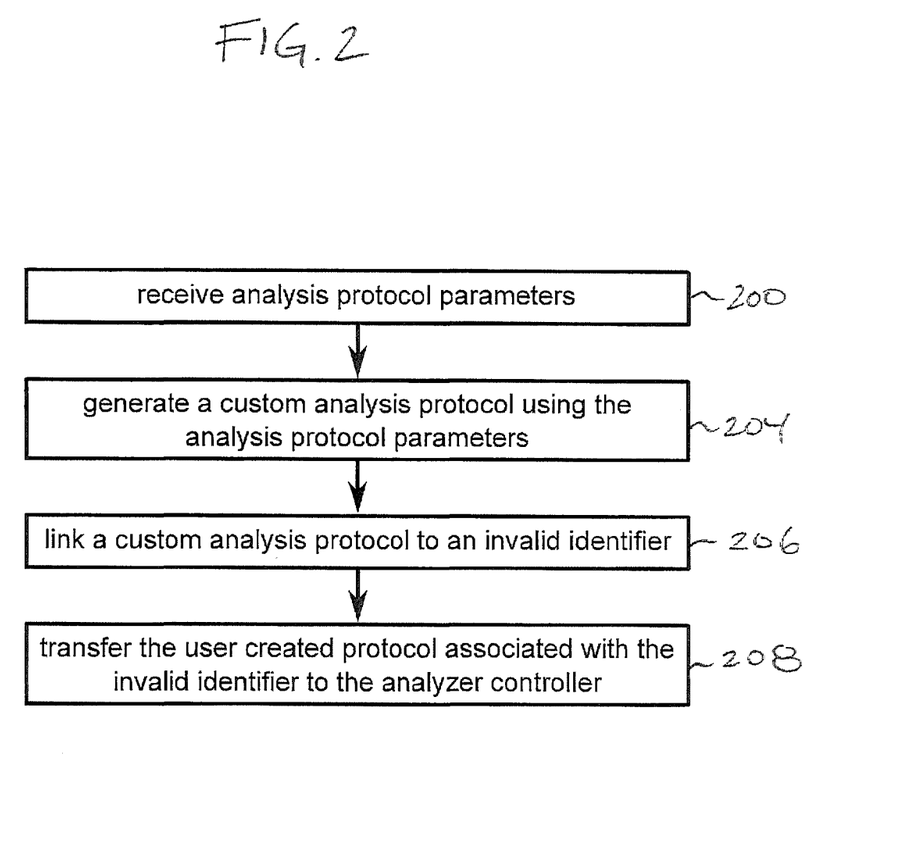
FIG. 2 shows a flowchart which illustrates steps performed by the protocol creation system of FIG. 1.

FIG. 2 shows a flowchart which illustrates steps performed by the protocol creation system 150 of FIG. 1. First in step 200 the analysis protocol parameters are received from the user interface. Next in step 204 a custom analysis protocol (UCAP) is generated using the analysis protocol parameters. Then in step 206 a link between a custom analysis protocol and the protocol identifier is formed. Finally in step 208 the user created protocol associated with the protocol identifier is transferred to the analyzer controller.

Figure 3:
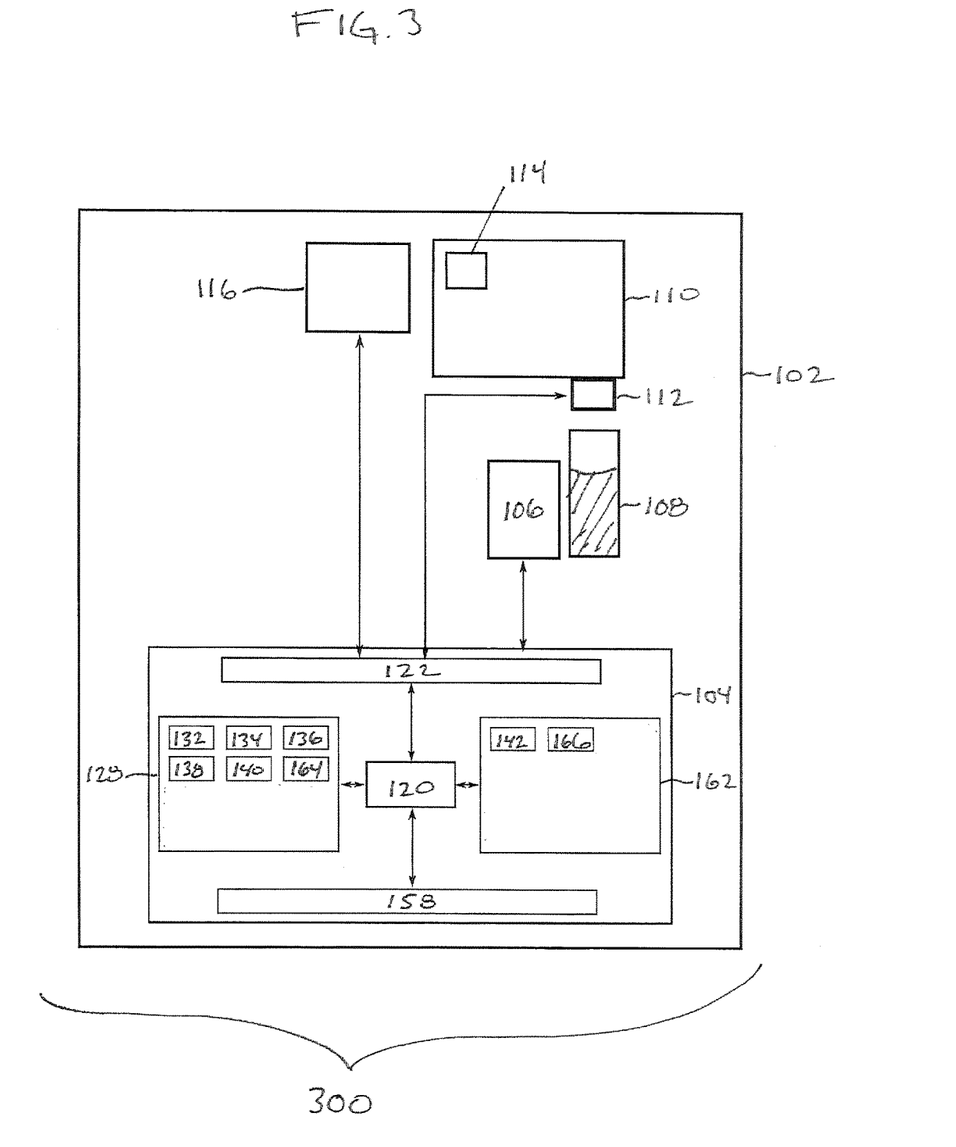
FIG. 3 shows a further example of an analysis system.

FIG. 3 shows a further example of an analysis system 300. The embodiment shown in FIG. 3 is similar to that shown in FIG. 1. However, in this case the analyzer controller 104 and the protocol creation system 150 of FIG. 1 have been combined into a single analyzer controller 104. The contents of the computer storages 128 and 160 in FIG. 1 have been merged and the contents of the computer memory 130 and 162 have also been merged. The user interface 158 for entering the analysis protocol parameters 164 is also now part of the analyzer controller 104.

Figure 4:
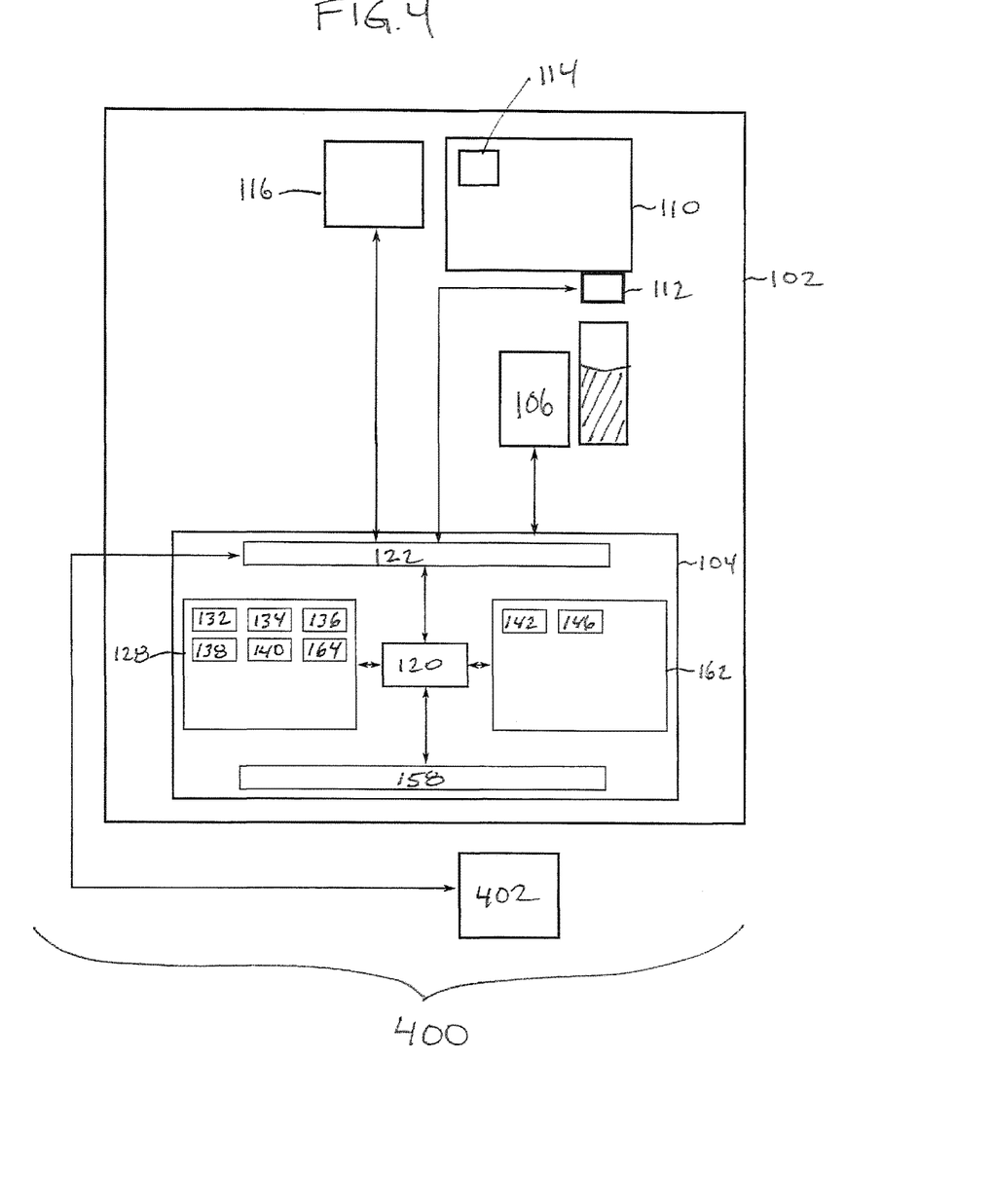
FIG. 4 shows a further example of an analysis system.

FIG. 4 shows a further example of an analysis system 400. The analysis system 400 is similar to the analysis system 300 shown in FIG. 3. However, in FIG. 4 there is additionally an identification tag generator 402. The identification tag 402 may be used to create and/or program the identifier 114 on the cartridge 110. For instance the identification tag generator 402 may in some embodiments contain a barcode generator and/or an RFID chip programmer.

Figure 5:
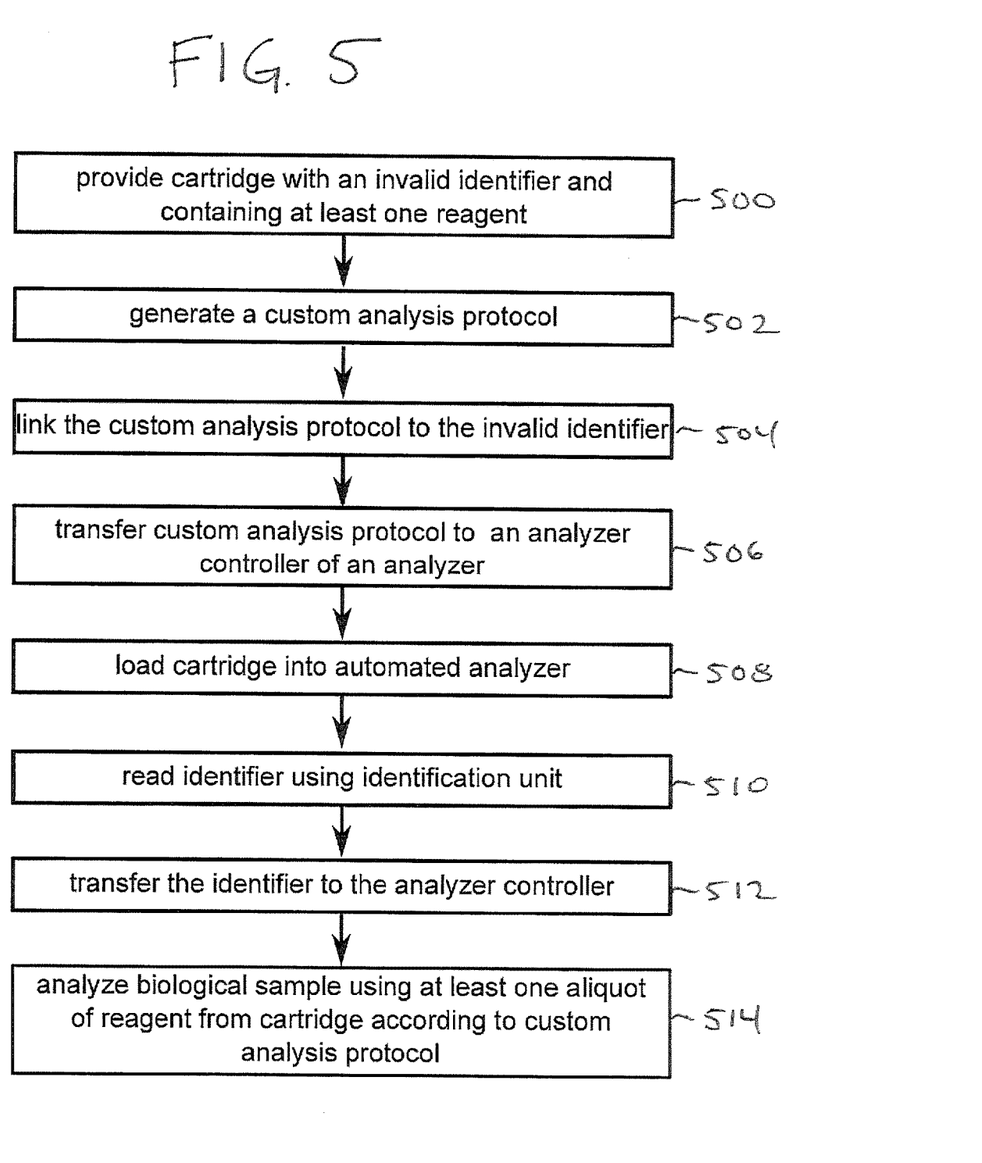
FIG. 5 shows a flowchart which illustrates a method.

FIG. 5 shows a flowchart which illustrates a method. First in step 500 a cartridge with an invalid identifier is provided and the cartridge contains at least one reagent. Next in step 502 a custom analysis protocol (UCAP) is generated. Then in step 504 the custom analysis protocol is linked to the invalid identifier. At this point the invalid identifier becomes a valid identifier. Whenever the identifier is encountered by an analysis system the analysis protocol will be recalled and may be used to analyze a biological sample. Next in step 506 the custom analysis protocol is transferred to an analyzer controller of an analyzer. Optionally, in step 508 the custom analysis protocol is selected. Next in step 510 a cartridge is loaded into the automatic analyzer. In step 512 the identifier is read using an identification unit. In some embodiments the identifier is transferred to the analyzer controller, for example by a network connection. The identifier of the cartridge is linked to the custom analysis protocol so the analyzer controller is thereby able to recall the custom analysis protocol for analyzing the biological sample. Finally in step 514 the biological sample is analyzed using the at least one aliquot a reagent from the cartridge and this is done in accordance to the custom analysis protocol.

Diagnostic laboratories need a high flexibility to run their own assays on a fully integrated high throughput analytical system. For example laboratories may develop assays for varying flu epidemics. The present invention may provide for a utility channel workflow or UCW which allows the consumer to run their own assays on a system which reports sample pipetting from a primary/secondary tube, isolation of nucleic acids from samples, preparation of specific PCR-mixture, amplification and detection, calculation and export of intermediate results, reporting the results, and release of results to an LIS system. LIS is a laboratory information system. Important aspects of the utility channel workflow are the definition and installation of customer defined assay parameters including cartridge IDs on the analytical system.

Figure 6:
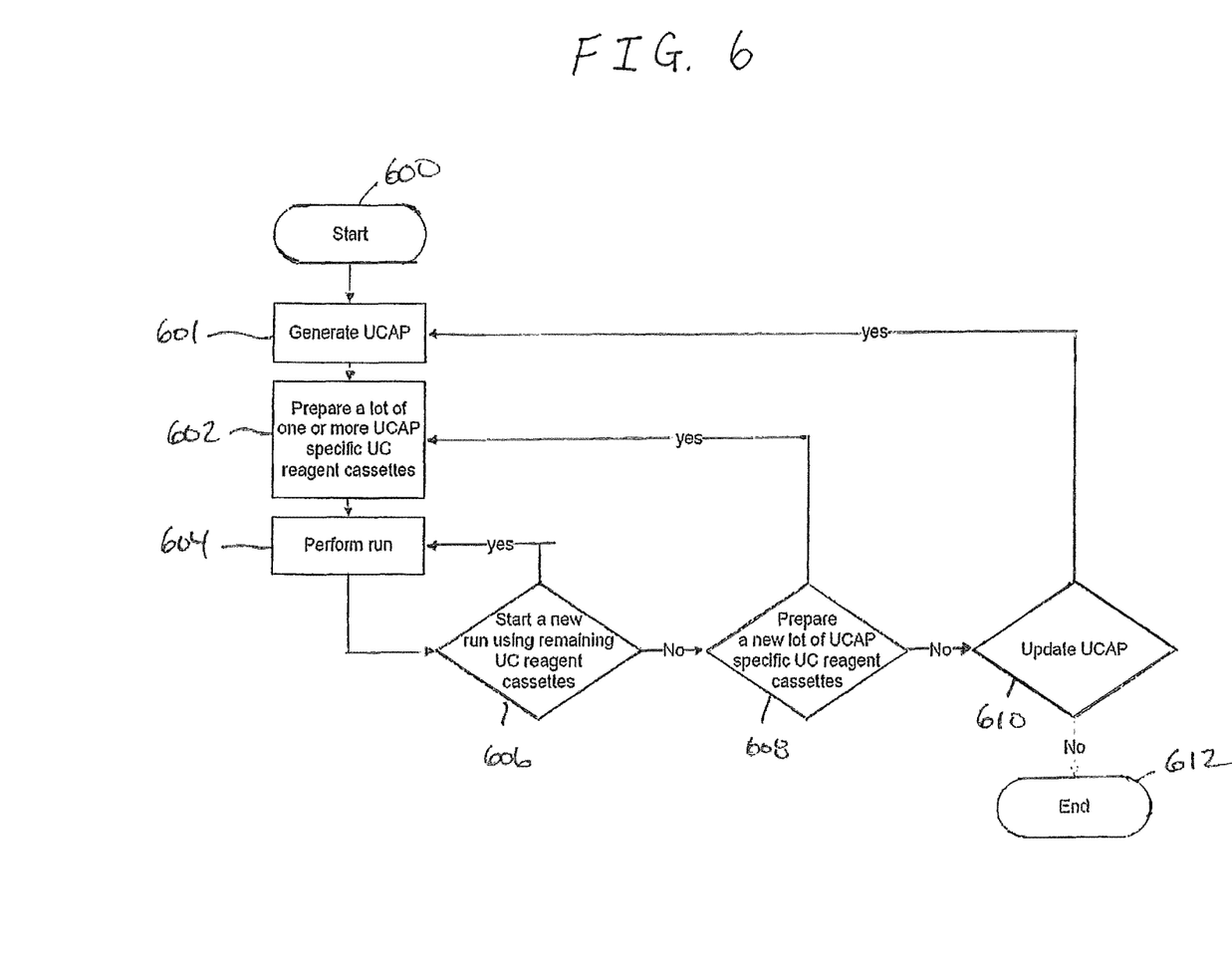
FIG. 6 shows a method of developing a custom utility channel workflow.

FIG. 6 shows a flow diagram which illustrates this process. First the method starts with step 600. Next in step 601 a custom analysis protocol (UCAP) is. Next in step 602 a lot of one or more custom analysis protocol specific UCW cartridges are prepared. Then in step 604 a run is performed where a biological sample is measured. In step 606 is a decision box. The question is to start a new run using the remaining UCW cartridges. If the answer is yes then step 604 is performed again. If not then the question proceeds to step 608 and the question is prepare a new lot of custom analysis protocol specific UCW cartridges. If the answer is yes then step 602 is performed again. If the answer is no then step 610 is performed which is also a question box. The question is should the custom analysis protocol be updated. If the answer is yes then the method returns back to step 601. If no then the method ends in step 612.

The important aspects of the utility channel workflow are the definition and installation of customer defined assay parameters including cartridge IDs on the analytical system. This corresponds to step 601 in FIG. 6. The appropriation of a customized cartridge corresponds and the labeling of the customer cartridge with the cartridge corresponds to step 602 in FIG. 6. The loading of the customized cartridge to run the customer defined assay on the system corresponds to step 604 in FIG. 6.

Figure 7:
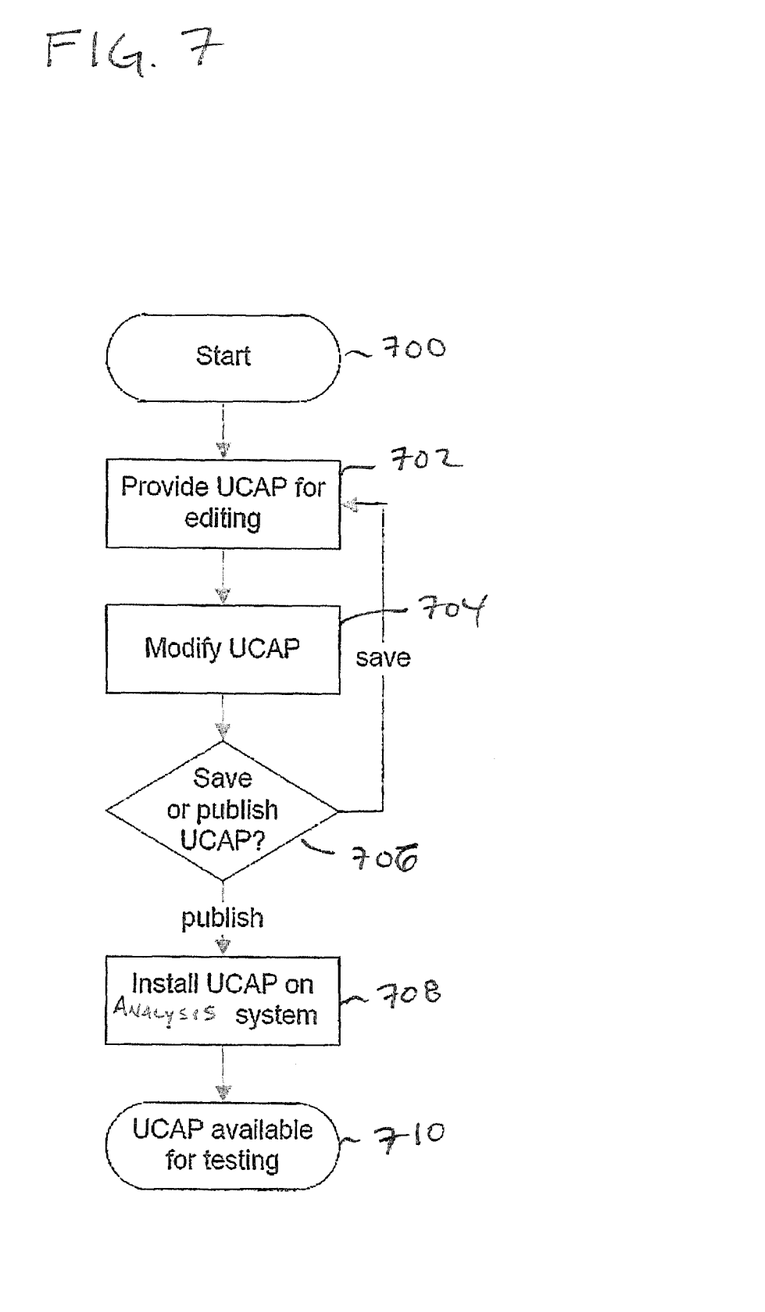
FIG. 7 shows a flowchart which illustrates how to perform step 601 of FIG. 6.

FIG. 7 shows a flowchart which illustrates how to perform step 601 of FIG. 6 in greater detail. That is how to generate the custom analysis protocol. The custom analysis protocol or utility channel analysis package contains all the necessary assay parameters to perform the sample processing, amplification, detection and calculation of intermediate results. The operator can generate the custom analysis protocol using a UCW tool or utility channel tool which is a separate software on a consumer PC in some embodiments. After generating the custom analysis protocol the operator is able to save the custom analysis protocol for further modification or to export the custom analysis protocol from the UCW tool to the analytical system. This is demonstrated in FIG. 7. First in step 700 the method starts. Next in step 702 a custom analysis protocol for editing is provided. Next in step 704 the custom analysis protocol is modified. Step 706 is a decision box and the question is should the custom analysis protocol be saved or published. If it is just saved then the method repeats the step 702. If it is decided to publish then the method proceeds to step 708. In step 708 the custom analysis protocol is installed on a analysis system. Finally in step 710 the custom analysis protocol is made available for testing. In step 704 the custom analysis protocol is modified.

A few of the basic parameters which may be defined by the operator may be the custom analysis protocol ID or identification which is equivalent to the identifier, the UCW cartridge ID. This identification may be used to link to the custom analysis protocol to an operator defined cartridge formulation. The operator may also define the channel target assignment, the IC validity range, the sample type and sample processing input volume, the PCR profile and also possibly the calculation sensitivity.

Figure 8:
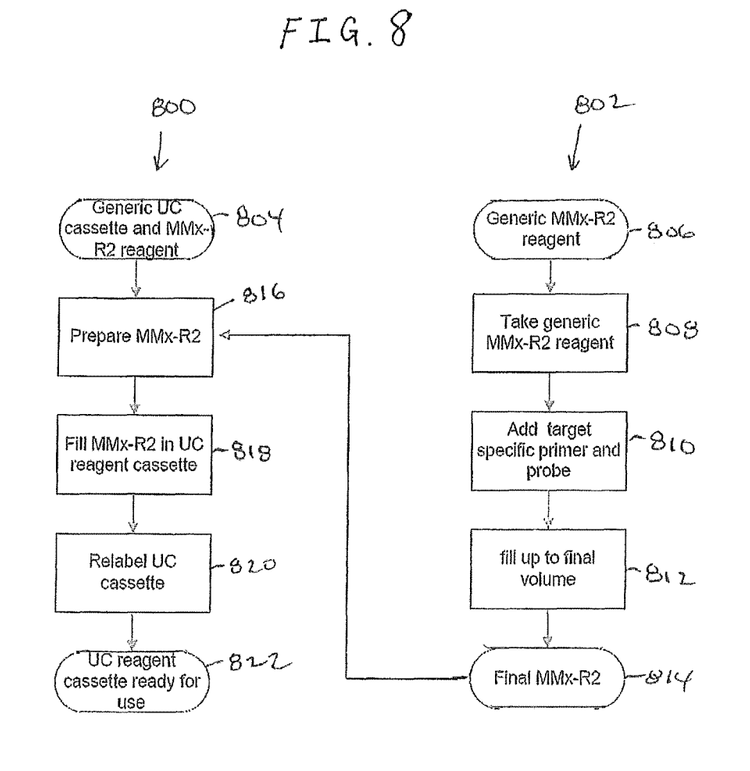
FIG. 8 shows a flow diagram which illustrates step 602 of FIG. 6 in greater detail.

FIG. 8 shows a flow diagram which illustrates the step 602 in FIG. 6 in greater detail. The flowchart in FIG. 8 is broken into two parts. The first part 800 shows the preparation of a custom analysis protocol specific cartridge. The second part 802 illustrates the preparation of a customized PCR master mixture which is used in some embodiments. The method starts in step 804 with a generic utility channel cartridge and a PCR master mix reagent (MMX-R2) without primers and probe. Step 806 is then performed from the section 802 of the flowchart. In step 806 a generic MMX-R2 reagent is prepared. Next in step 808 take the generic MMX-R2 reagent and add 810 target specific primers and probe. In step 812 the cartridge is filled up to a final volume. In the final step 814 the final MMX-R2 is prepared. Step 804 then proceeds to step 816, which receives the final MMX-R2 mixture prepared in step 814.

Next in step 818 the cartridge is filled with the MMX-R2 into the utility channel cartridge. Next in step 820 the utility channel cartridge is relabeled. Finally in step 822 the utility channel cartridge is ready for use. Essentially the UCW includes the use of generic PCR master mixtures, MMX-R2 reagent which does not contain target specific primers, and a generic utility channel cartridge, based on the generic concept of the analytical system. The operator can prepare a custom analysis protocol specific cartridge by adding his target specific primers to the generic PCR master mixture and filling the customized PCR master mixture in the generic cartridge. This procedure is illustrated in FIG. 8.

Figure 9:
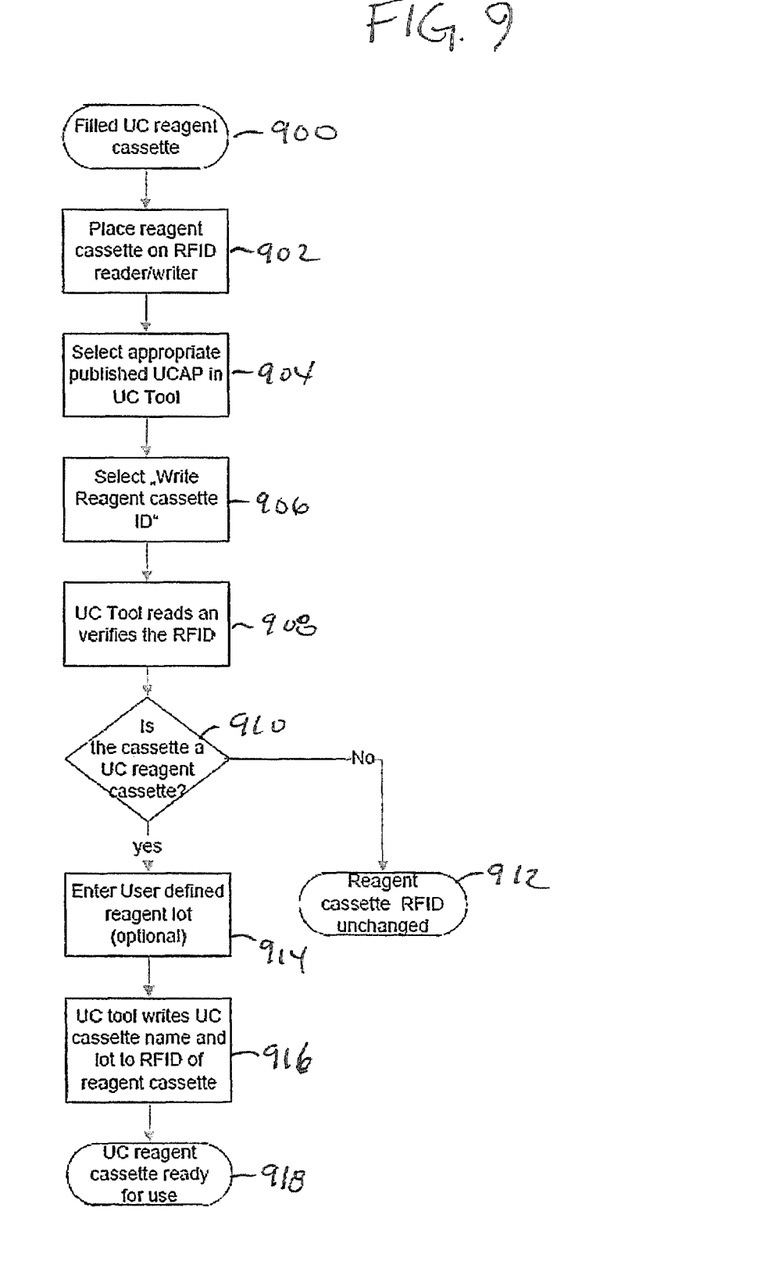
FIG. 9 shows a flowchart which illustrates the creation of custom utility channel cartridges.

FIG. 9 shows a flowchart which illustrates the filling of the utility channel cartridge. This corresponds to part of step 602 in FIG. 6. In order to use the custom analysis protocol specific cartridge in the fully integrated analytical system the UCW cartridge has to provide a corresponding identification tag to be recognized by the system. Two alternative labeling approaches are mentioned: first the UCW cartridge identifier will be written to an unprotected data area of the RFID or barcode and attached to the cassette using the UCW tool and a connected RFID or barcode writer. This is illustrated in FIG. 9. First in step 900 the filled UC reagent cassette is provided. Next in step 902 the cartridge is placed on an RFID reader and/or writer.

Next in step 904 an appropriate published custom analysis protocol is selected using the UCW tool. Next in step 906 a write identifier is selected. Next in step 904 the UCW tool reads and verifies the RFID. Step 910 is a decision box. The question is the cassette a UCW cartridge. If the answer is no then the cartridge RFID is unchanged and the method ends. If the answer is yes then a user defined reagent lot is entered in step 914. Next in step 916 the UCW tool is used to write the UCW cartridge name and lot to an RFID of the cartridge. Then finally in step 918 the UCW cartridge is ready for use.

Alternatively the unique identifier of the RFID chip can be used as an identification tag. The unique identifier of the RFID can be linked with the corresponding custom analysis protocol via a cross table deposited on the analytical system. The cross table, thus comprises the protocol identifier which permits an invalid identifier to be changed into a valid identifier. Finally when performing a run using the utility channel is similar to the standard workflow. The operator can load the analytical system with the custom analysis protocol specific cartridge, which is used in the same way that a cartridge containing a manufacturer provided assay. The UCW w uses the same bulk reagents and consumables.

LIST OF REFERENCE NUMERALS

100 analysis system
102 analyzer
104 analyzer controller
106 analytical unit
108 biological sample
110 cartridge
112 dispenser
114 identifier
116 identification unit
120 processor
122 hardware interface
124 network interface
128 computer storage
130 computer memory
132 cartridge database
134 analysis protocol database
136 identifier
138 custom analysis protocol
140 analysis result
142 control module
150 protocol creation system
152 processor
154 network interface
156 network connection
158 user interface
160 computer storage
162 computer memory 164 analysis protocol parameters
166 analysis protocol creation module
300 analysis system
400 analysis system
402 identification tag generator

The invention claimed is:

1. A method of analyzing a biological sample in an automated analysis system comprising an analyzer, wherein said analyzer is configured for accepting a cartridge with a valid identifier and rejecting a cartridge with an invalid identifier, comprising the steps of:
  (a) providing a cartridge comprising an invalid identifier and containing at least one reagent for analyzing the biological sample;
  (b) receiving analysis protocol parameters from a user interface, wherein said analysis protocol parameters are selected from the group consisting of an analysis protocol identifier, a cartridge identifier, a channel target assignment, an internal control validity range, a sample type, a sample process input volume, a polymerase chain reaction profile, a calculation sensitivity, dilution factors, incubation time, reagent addition, volumes, temperature settings, washing steps and combinations thereof;
  (c) generating a custom analysis protocol using the analysis protocol parameters received in step (b) with a protocol creation system, wherein steps (a) through (c) are interchangeable or may be performed in parallel;
  (c) linking the custom analysis protocol to a protocol identifier corresponding to the invalid identifier;
  (d) appending the custom analysis protocol to a set of analysis protocols in an analyzer controller of the analyzer, and thereby changing an invalid identifier on the cartridge into a valid identifier such that the analyzer controller accepts the cartridge;
  (e) selecting said custom analysis protocol linked to the protocol identifier corresponding to the valid identifier;
  (f) loading said cartridge into said automated analyzer;
  (g) reading said identifier, wherein the identifier is read by an identification unit comprising an identifier reader comprised in the analyzer; and
  (h) analyzing said biological sample using at least one aliquot of said at least one reagent comprised in said cartridge according to the selected custom analysis protocol.

2. The method of claim 1, wherein the identifier is comprised on an identification tag.

3. The method of claim 1, wherein the identifier is a unique identifier on the identification tag, and the controller memory comprises a cross-table comprising protocol identifiers corresponding to unique identifiers which assigns a unique identifier to an analysis protocol.

4. The method of claim 2, wherein the identifier is generated on an identification tag by an identifier generator and the custom analysis protocol is stored with a reference to the protocol identifier.

5. The method of claim 1, wherein said custom analysis protocol is created on a protocol creation system, and wherein the custom created analysis protocol is transferred from the analysis protocol creation system to the analyzer controller using a network connection, wherein the custom analysis protocol is referenced by the protocol identifier.

6. The method of claim 2, wherein said custom analysis protocol is created on a protocol creation system, and wherein the custom created analysis protocol is transferred from the analysis protocol creation system to the analyzer controller using a network connection, wherein the custom analysis protocol is referenced by the protocol identifier.

7. The method of claim 3, wherein said custom analysis protocol is created on a protocol creation system, and wherein the custom created analysis protocol is transferred from the analysis protocol creation system to the analyzer controller using a network connection, wherein the custom analysis protocol is referenced by the protocol identifier.

8. The method of claim 4, wherein said custom analysis protocol is created on a protocol creation system, and wherein the custom created analysis protocol is transferred from the analysis protocol creation system to the analyzer controller using a network connection, wherein the custom analysis protocol is referenced by the protocol identifier.

9. The method of claim 1, wherein said custom analysis protocol is created on a protocol creation system, and wherein the custom created analysis protocol is transferred from the analysis protocol creation system to the analyzer controller using a network connection, wherein the custom analysis protocol is referenced by the protocol identifier.

* * * * *